(12) United States Patent
Lee et al.

(10) Patent No.: US 12,210,012 B2
(45) Date of Patent: Jan. 28, 2025

(54) MONOLITHICALLY INTEGRATED AND DENSELY PACKED ARRAY SENSOR PLATFORM FOR ULTRA-LOW POWER GAS SENSING APPLICATIONS

(71) Applicant: North Carolina State University, Raleigh, NC (US)

(72) Inventors: Bongmook Lee, Raleigh, NC (US); Veena Misra, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 281 days.

(21) Appl. No.: 17/764,332

(22) PCT Filed: Oct. 2, 2020

(86) PCT No.: PCT/US2020/054102
§ 371 (c)(1),
(2) Date: Mar. 28, 2022

(87) PCT Pub. No.: WO2021/067756
PCT Pub. Date: Apr. 8, 2021

(65) Prior Publication Data
US 2022/0349871 A1    Nov. 3, 2022

Related U.S. Application Data

(60) Provisional application No. 62/910,639, filed on Oct. 4, 2019.

(51) Int. Cl.
*G01N 33/497*   (2006.01)
*G01N 33/00*   (2006.01)

(52) U.S. Cl.
CPC ....... *G01N 33/497* (2013.01); *G01N 33/0031* (2013.01)

(58) Field of Classification Search
CPC .................. G01N 33/0031; G01N 33/497
See application file for complete search history.

(56) References Cited

U.S. PATENT DOCUMENTS 6,326,315 B1 * 12/2001 Uchiyama ................ C30B 7/00
257/532
9,164,052 B1   10/2015 Speer et al.
(Continued)

FOREIGN PATENT DOCUMENTS

WO    WO-2019073483 A1 *  4/2019   ............. G01N 27/18

OTHER PUBLICATIONS

International Search Report and Written Opinion for International Application No. PCT/US2020/054012 mailed Jan. 8, 2021.

*Primary Examiner* — Justin N Olamit
(74) *Attorney, Agent, or Firm* — Thomas | Horstemeyer, LLP

(57) ABSTRACT

The present disclosure presents environmental sensing apparatuses and methods. In one such apparatus, an environmental sensor comprises a substrate and an array of multiple metal oxide materials on the substrate. The multiple metal oxide materials can comprise layers of different metal oxide material, in which the multiple metal oxide materials are deposited on a cross-bar array of heater elements and electrodes and each row in the cross-bar array contains an independently-controlled heater element and each column in the array contains a pair of electrodes. At each crossing of the heater element and the pair of electrodes, one of the multiple metal oxide materials is deposited, and the pair of electrodes and the heater elements are dielectrically isolated from one another at the crossing.

10 Claims, 11 Drawing Sheets

(56) References Cited

U.S. PATENT DOCUMENTS

| | | | | |
|---|---|---|---|---|
| 9,625,401 B2* | 4/2017 | Whitten | ................ | G01N 25/20 |
| 10,466,190 B1* | 11/2019 | Ancona | ................ | G01N 27/227 |
| 2002/0142478 A1 | 10/2002 | Wado et al. | | |
| 2008/0134753 A1 | 6/2008 | Jun et al. | | |
| 2011/0262117 A1* | 10/2011 | Yamazaki | ................ | C30B 33/00 |
| | | | | 392/416 |
| 2014/0260546 A1* | 9/2014 | Chen | ................ | G01N 33/0031 |
| | | | | 73/31.06 |
| 2016/0198984 A1* | 7/2016 | Daniele | ................ | D21H 27/30 |
| | | | | 427/121 |

* cited by examiner

MONOLITHICALLY INTEGRATED AND DENSELY PACKED ARRAY SENSOR PLATFORM FOR ULTRA-LOW POWER GAS SENSING APPLICATIONS

CROSS-REFERENCE TO RELATED APPLICATIONS

This application is the 35 U.S.C. § 371 national stage application of International Application No. PCT/US2020/054012, filed Oct. 2, 2020, which claims priority to U.S. provisional application entitled, "Novel and Highly Scalable Multi-Material Metal Oxide Array Gas Sensors," having Ser. No. 62/910,639, filed Oct. 4, 2019, which is entirely incorporated herein by reference.

STATEMENT REGARDING FEDERALLY SPONSORED RESEARCH OR DEVELOPMENT

This invention was made with government support under grant number 1160483 awarded by the National Science Foundation. The government has certain rights in the invention.

TECHNICAL FIELD

The present disclosure is generally related to metal oxide sensors.

BACKGROUND

Active sensing materials are typically created using a chemical process that is not suitable and compatible for large-scale fabrication or high volume manufacturing lines. Current commercial metal oxide sensors are discrete devices and hence are difficult to integrate with control electronics. For example, current environmental sensors uses single sensing material in a large area (>300 µm×300 µm). In order to make an environmental sensing system, different sensing materials are needed. As a result, current portable sensing systems are bulky and not scalable due to the integration of each large area sensor. Another problem of the current state-of-the-art commercial metal oxide sensors is that a sensor requires electrical heating to a large active area resulting in high power consumption. This high power consumption is a big barrier for wide adoption of gas sensor technologies for portable and wearable applications.

SUMMARY

Embodiments of the present disclosure provide environmental sensing apparatuses and methods. One such environmental sensor comprises a substrate; and an array of multiple metal oxide materials on the substrate, wherein at least one of the multiple metal oxide materials comprises layers of different metal oxide material, the multiple metal oxide materials are deposited on a cross-bar array of heater elements and electrodes, and each row in the cross-bar array contains an independently-controlled heater element and each column in the array contains a pair of electrodes. At each crossing of the heater element and the pair of electrodes, one of the multiple metal oxide materials is deposited, and the pair of electrodes and the heater elements are dielectrically isolated from one another at the crossing.

The present disclosure can also be viewed as an environmental sensing method. In this regard, one embodiment of such a method, among others, can be broadly summarized by forming an array of multiple metal oxide materials on a substrate, wherein at least one of the multiple metal oxide materials comprises layers of different metal oxide material, the multiple metal oxide materials are deposited on a cross-bar array of heater elements and electrodes, and each row in the cross-bar array contains an independently-controlled heater element and each column in the array contains a pair of electrodes. At each crossing of the heater element and the pair of electrodes, one of the multiple metal oxide materials is deposited, and the pair of electrodes and the heater elements are dielectrically isolated from one another at the crossing. The method further comprises applying a particular temperature to one of the multiple metal oxide materials by individually controlling a row of the heater elements on which the one of the multiple metal oxide materials is positioned.

In one or more aspects for such apparatuses and/or methods, at least one of the multiple metal oxide materials is sensitive to a presence of a particular gas substance; at least one of the multiple metal oxide materials responds to the presence of the particular gas substance by demonstrating a change in electrical resistance, surface ionization, optical, or magnetic parameters that can be measured; the at least one of the multiple metal oxide materials intermixes the layers of different metal oxide materials at a particular temperature applied by a particular row of the heater elements; another one of the multiple metal oxide materials intermixes at a different temperature applied by a different row of the heater elements; the substrate is a stretchable substrate formed of Nanocellulose; the substrate is a single silicon wafer, wherein the array of multiple metal oxide materials on the substrate comprise at least 15 metal oxide gas sensors; an exemplary method includes applying a different temperature to another one of the multiple metal oxide materials by individually controlling a different row of the heater elements on which the other one of the multiple metal oxide materials is positioned; and/or a thickness of top metal oxide materials can be modified so that the sensing responses are changed.

In one or more aspects for such apparatuses and/or methods, the array of multiple metal oxide materials comprise at least a first metal oxide material having first layers of metal oxide material and a second metal oxide material having second layers of metal oxide material that is different from the first layers of metal oxide material, wherein the first metal oxide material produces a response to a first analyte that is different from a response to the first analyte by the second metal oxide material; wherein a number of the first layers is different from a number of the second layers; and/or the first layers of metal oxide material is configured to be activated at a first temperature, wherein the second layers of metal oxide material is configured to be activated a second temperature that is different from the first temperature.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

High power consumption is a big barrier for wide adoption of environmental sensor technologies for portable and wearable applications. In accordance with embodiments of the present disclosure, micro-scale gas sensors array and sensing material are activated by localized heating. Such technology provides highly integrated and scaled single chip metal oxide gas sensor arrays for multiple gas detection compared to a large and bulky gas sensor system, which can be used for wearable or portable sensing applications, among others. This also can be used for health applications in medical devices as well as Internet of Things (IOT) sensors. The Internet of Things (IOT) bears the promise of connecting numerous sensor nodes with each other along with cloud platforms to manage and process large amounts of data.

An exemplary novel approach provides a manufacturable pathway to achieve monolithic integration of multiple metal oxide materials along with MEMS (Micro-Electro-Mechanical Systems) based heaters in a dense array leading to ultimate selectivity, low cost, and manufacturability compatibility with a CMOS (complementary metal-oxide-semiconductor) backend foundry process. By integrating MEMS heaters and multiple sensing materials in arrays, such as $SnO_2$, CuO, SnO, ZnO, SnTiO, NiO, $Ga_2O_3$, $MoO_3$, Si-doped $SnO_2$ (or ZnO), Pt-doped $SnO_2$ (or ZnO), different operating temperatures can be applied to the same sensing material or the same temperature can be applied to different sensing materials to achieve optimal selectivity through data analysis.

Figure 1:
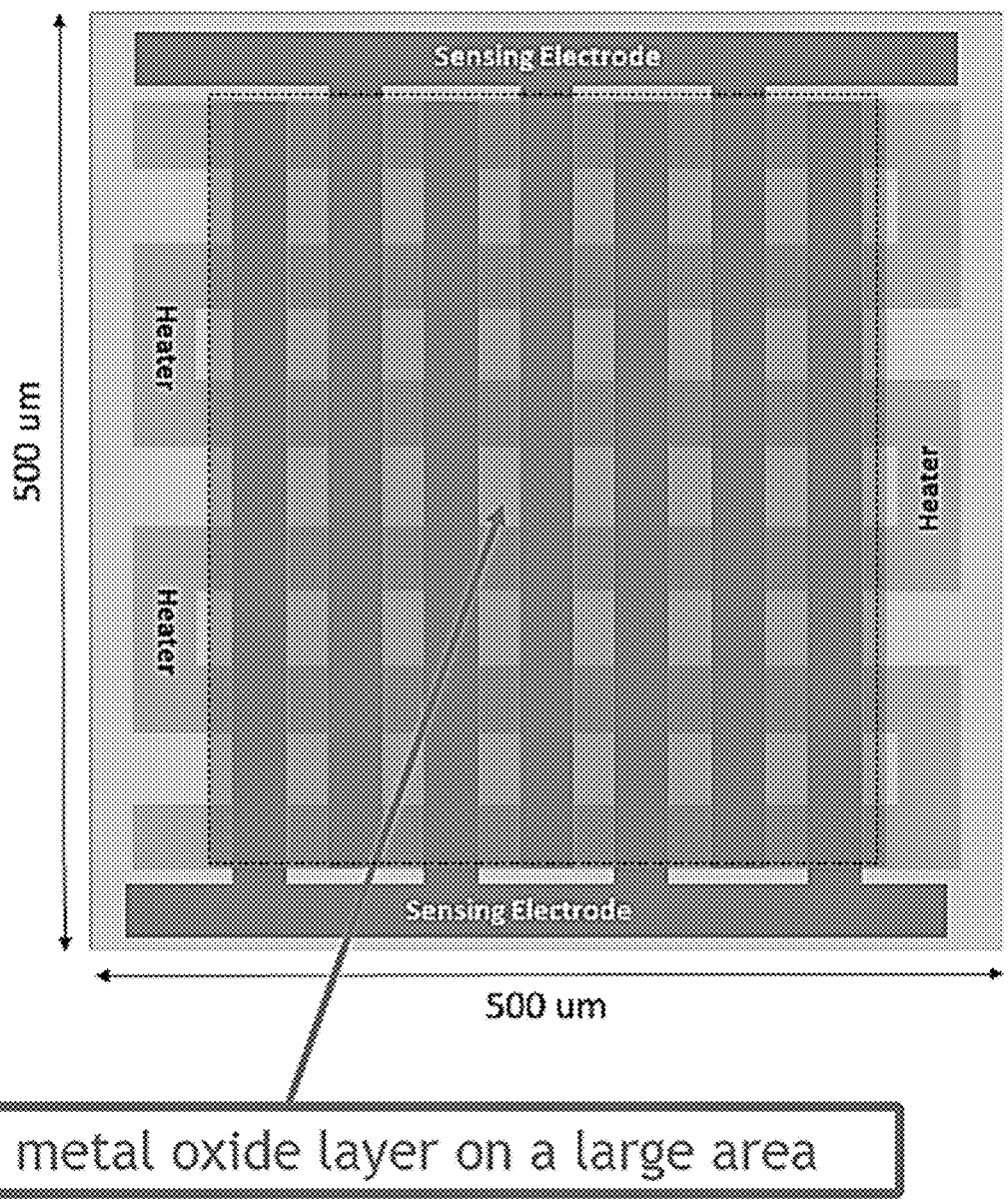
FIG. 1 is a top-view diagram of an environmental sensor design in a conventional approach for a single environmental sensor.
Figure 2:
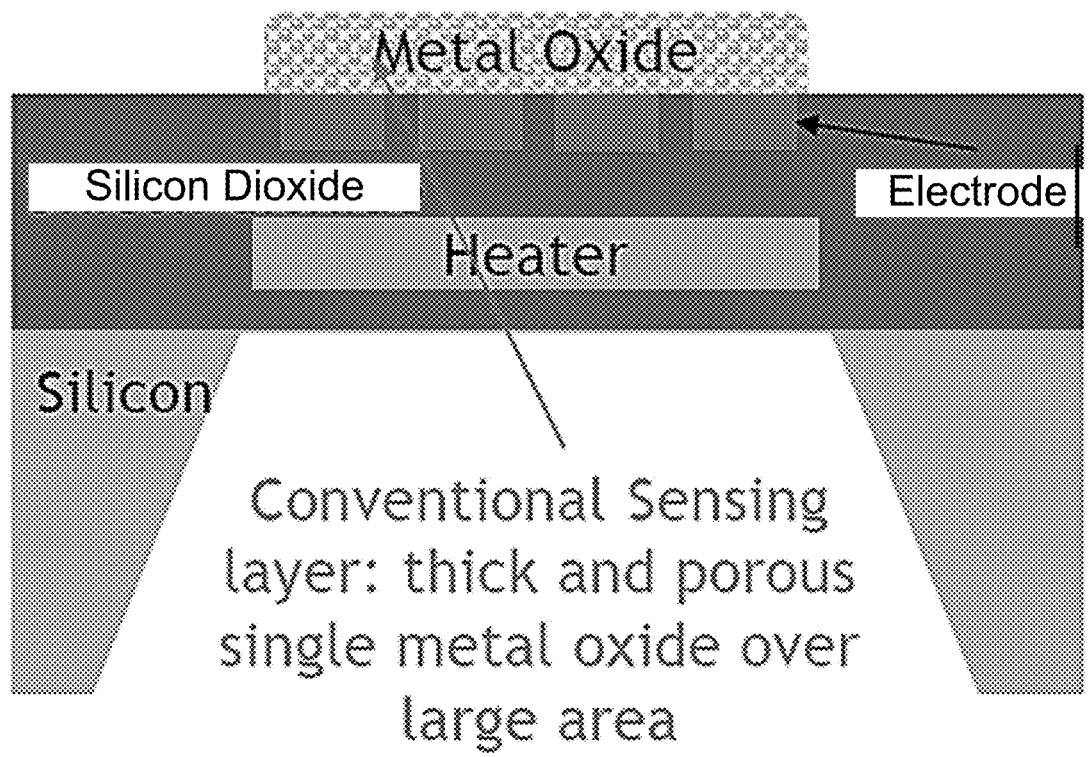
FIG. 2 is a side-view diagram of the environmental sensor design of FIG. 1.

While active sensing materials are typically created using a chemical process that is not suitable and compatible for large-scale fabrication or high volume manufacturing lines, embodiments of the present disclosure are based on current Si processing so the sensors and control electronics can be integrated on a wafer scale resulting in much smaller system as compared to current sensor systems. For comparative analysis, FIG. 1 presents a top-view and FIG. 2 presents a side-view of an environmental sensor design in a conventional approach for a single sensor. In the figures, a thick and porous single metal oxide layer is provided over a large area (e.g., >300 µm×300 µm, such as 500 µm×500 µm). The single metal oxide layer is situated over a single heater element resulting in high power consumption due to electrical heating across the large area of the metal oxide layer.

Figure 3:
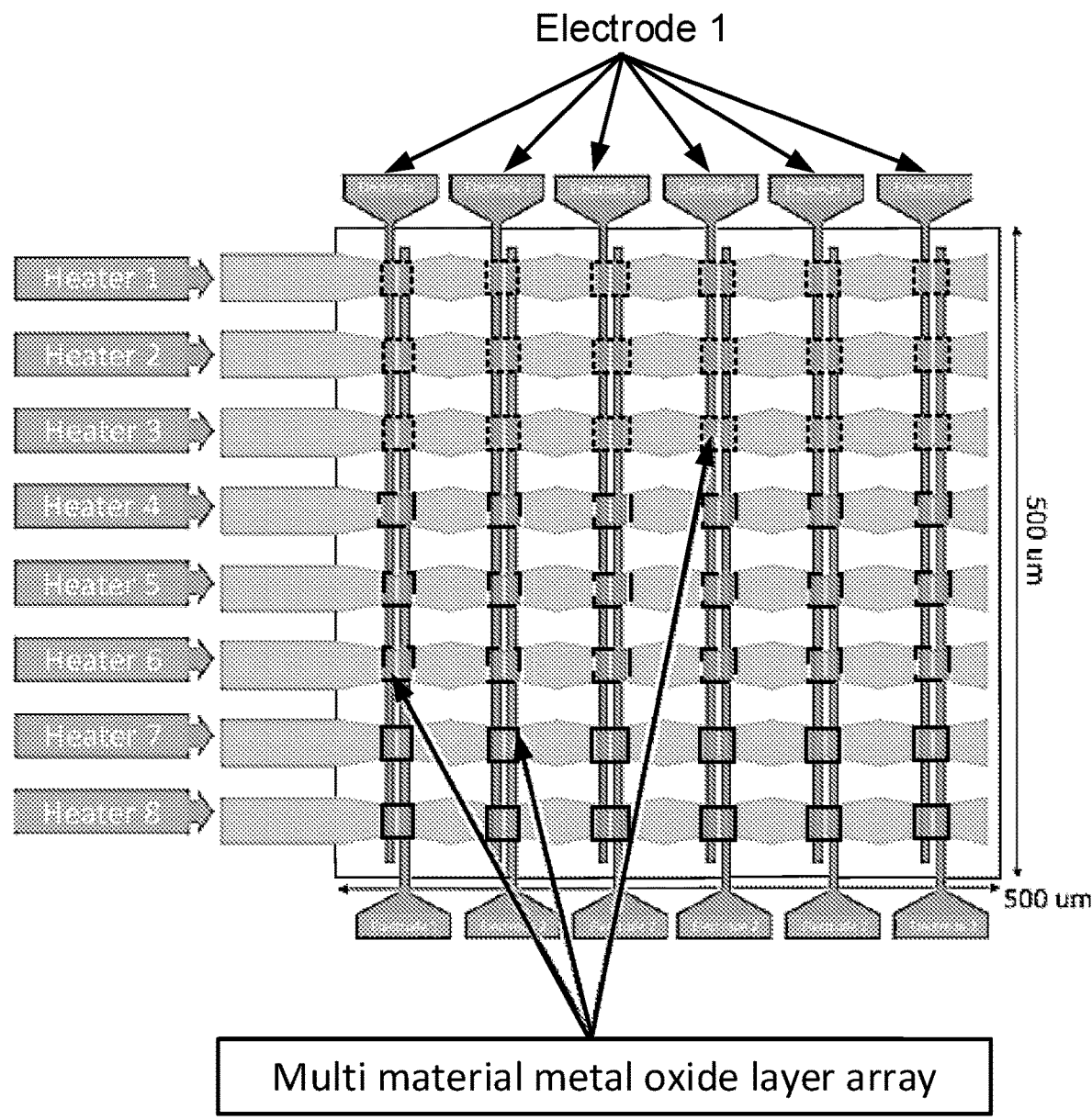
FIG. 3 is top-view diagram of an embodiment of an environmental sensor design for multiple environmental sensors in accordance with embodiments of the present disclosure.
Figure 4:
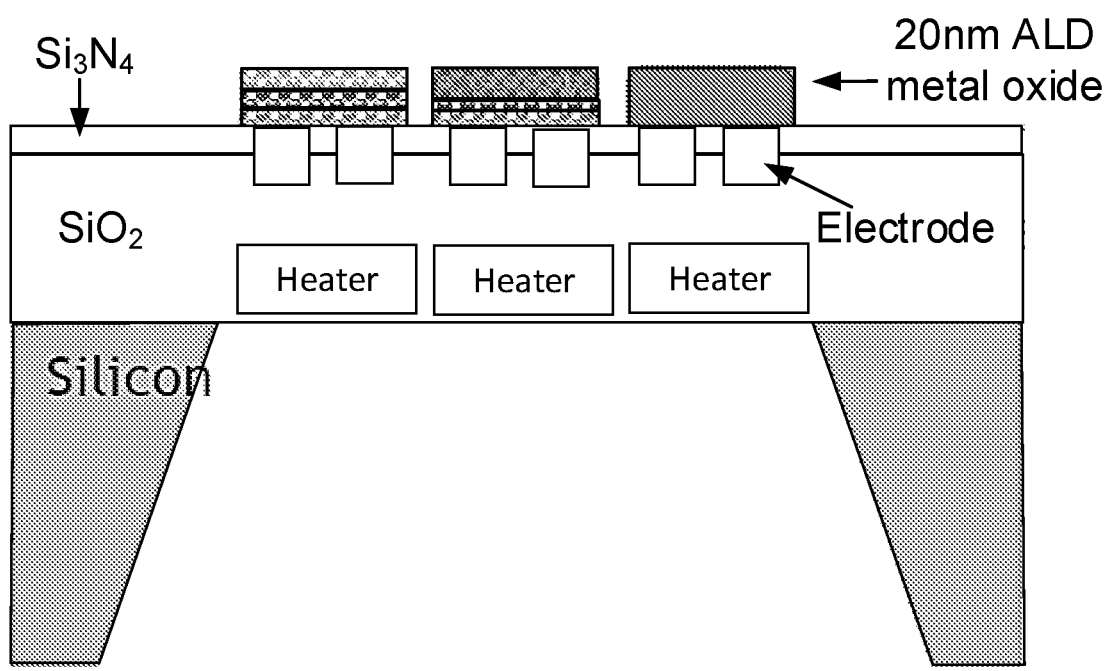
FIG. 4 is side-view diagram of the environmental sensor design of FIG. 3.

Next, FIG. 3 presents a top-view and FIG. 4 presents a side-view of an environmental sensor design for multiple sensors in accordance with various embodiments of the present disclosure. In the figures, a multi-material metal oxide layer array is provided over a large area (e.g., 500 µm×500 µm). In contrast to having a single and thick (>100 nm) metal oxide layer, multiple and ultrathin metal oxide layers (e.g., less than 20 nm thick in one embodiment) are formed with selective ALD (Atomic Layer Deposition) metal oxide deposition, in one embodiment. Accordingly, such a miniaturized gas sensing array can be fabricated in commercial Si or MEMS foundry and is easily embedded into the back-end process. In various embodiments, an exemplary sensing array can be fabricated on flexible and stretchable substrate (e.g. Nanocellulose).

As shown in FIG. 3, multiple heater elements and sensing electrodes can be arranged under the metal oxide layer(s) using a cross-bar sensing array, where each row in the array contains a heater element and each column in the array contains a pair of electrodes. In FIG. 3, the first top three rows of the multi-material metal oxide layer array are shown to include the same metal oxide layer material (as represented by the dashed boxes), where the next three rows have a different metal oxide layer material (as represented by the segmented boxes) and the last two rows have a further different metal oxide layer (as represented by the solid boxes). Accordingly, each of the different metal oxide layer materials may produce a different response to an analyte, in various embodiments. Thus, multiple environmental sensors can be fabricated on a single Si wafer in accordance with embodiments of the present disclosure.

As shown in FIG. 4, in one embodiment, sensors may use two electrodes that are located in close proximity to each other and can be biased individually. During operation, a power supply can be coupled to one of the electrodes and a current can be measured externally and evaluated to determine the presence of a particular substance or analyte, such as by detecting a change in electrical resistance.

Figure 5:
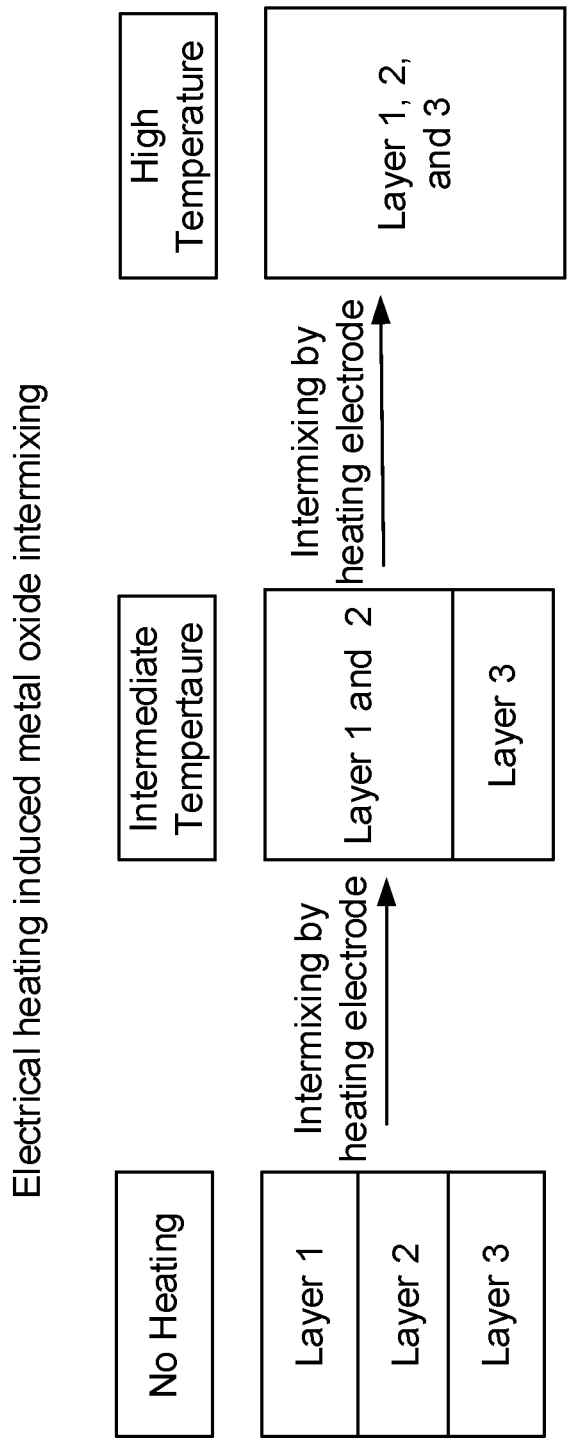
FIG. 5 is a diagram showing intermixing of metal oxide layers within a cross-bar sensing array in accordance with various embodiments of the present disclosure.
Figure 6A:
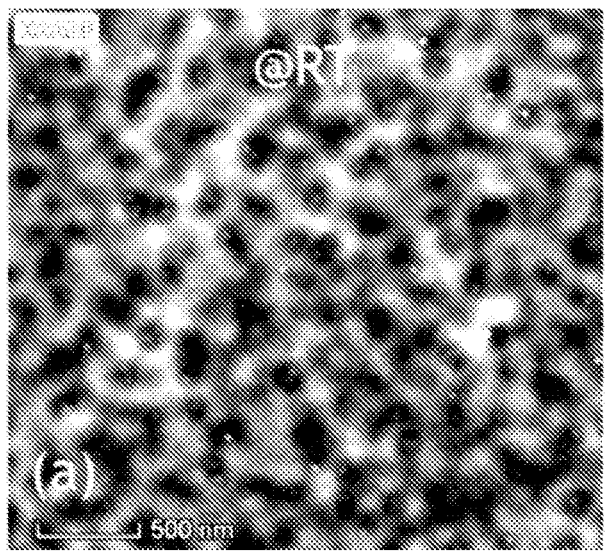
FIGS. 6A-6E are electron microscopy images of the surface of $SnO_2$—ZnO composites across the annealed temperature range of 25° C. to 900° C. for an exemplary environment sensor in accordance with embodiments of the present disclosure.
Figure 6B:
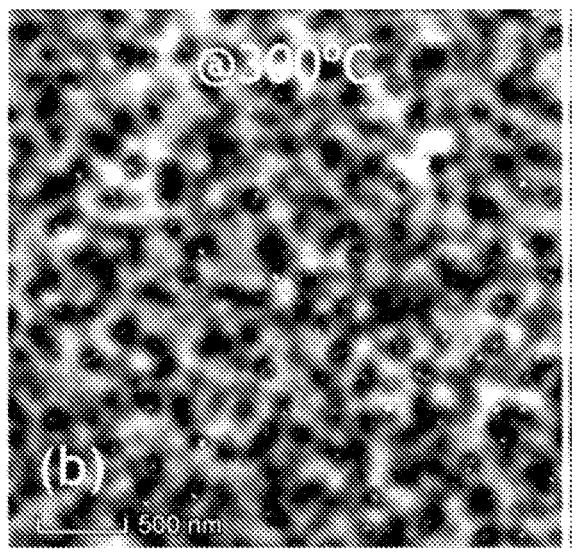
Figure 6C:
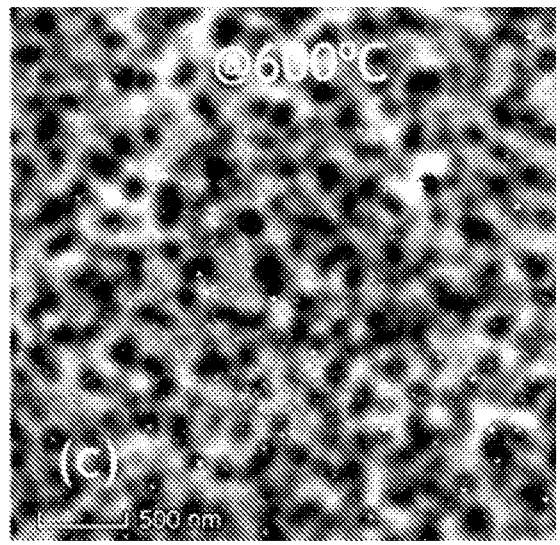
Figure 6D:
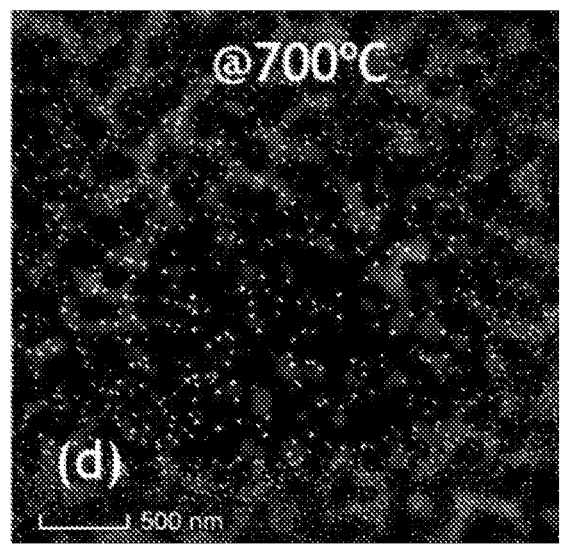
Figure 6E:
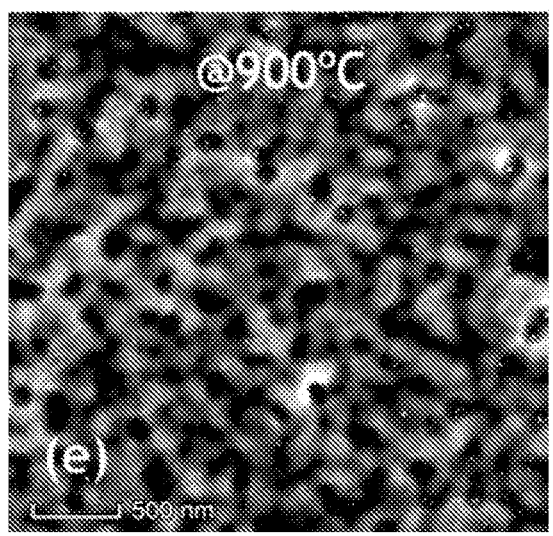

By fabricating such a cross-bar sensing array, one heater element, one row of heater elements, and/or one column of heater elements can be individually controlled. Thus, as demonstrated in FIG. 5, a metal oxide composite can be formed via localized heating. In this example, three metal oxide layers (layer 1, layer 2, and layer 3) have been deposited within an exemplary sensing array. By application of an intermediate temperature by a localized heater, a composite of two or more layers, such as layer 1 and layer 2, may be formed via intermixing induced by the local heater. Accordingly, an operational temperature corresponding to the intermediate temperature may activate layer 1 and layer 2 (and not layer 3), in some embodiments. Further, at an elevated or high temperature, all three layers may be activated by localized heating as represented in FIG. 5. As such, the interactions of gases and a metal oxide composite can be locally activated.

Thus, a fabrication process in accordance with various embodiments of the present disclosure allows for selective annealing, where under the same stack deposition conditions, such selective annealing is not possible for a conventional sensor array fabrication process. As seen in the TEM (transmission electron microscopy) Images of FIGS. 6A-6E, with a rise in anneal temperature, an exemplary ALD metal oxide system in accordance with the present disclosure appears to be progressively diffusing, first among the two metal oxide layers at lower temperatures and then into the $SiO_2$ layer at higher temperatures. An XPS (X-ray photoelectron spectroscopy) survey of the samples' surface in % atomic values as seen in Table 1 (below) corroborate the inter-mixing of oxide stack as seen from the TEM images.

TABLE 1

Atomic % values as obtained from the XPS survey rounded off to the nearest whole number.

| Anneal Cond. | Atomic % | | | |
|---|---|---|---|---|
| | Sn | Zn | O | Si |
| As-deposited | 24 | 11 | 65 | 0 |
| 300° C. Anneal | 24 | 10 | 66 | 0 |
| 600° C. Anneal | 33 | 1 | 66 | 0 |
| 900° C. Anneal | 19 | 0 | 65 | 16 |
| 1200° C. Anneal | 1 | 0 | 61 | 38 |

XPS used in this experiment picks the signal from the top 10 nm from the sample's surface, so it presents a good picture of the inter-diffusion going on in the ALD metal oxide layers, as the total ALD stack thickness is ~16 nm. Change in crystallinity of the ALD layers is also seen from both the TEM images. It is evident that for samples annealed at 600° C. and 900° C., well-formed crystal planes appear, while they do not appear as significant at other temperatures. Upwards at 900° C., it appears that the resistance to the diffusion of Sn—O—Zn in $SiO_2$ decreases and we see a greater surface concentration of Si.

Intermixing of metal oxide layers can result in either an increase or a decrease of the sensory response for individual sensors. Thus, by varying the temperature of a metal oxide composite sensor via localized heating, the inherent characteristics of the sensor can be individually changed and tailored for detection of various substances, such as gases. An array of sensors may then be configured with each showing a different response to various gases, such as a change in electrical resistance, surface ionization, optical, or magnetic parameters. Accordingly, an embodiment of an environmental sensor device can feature an exemplary array of sensors, in which individual sensors can be tuned using a localized heater. As such, the sensing performance and selectivity of a sensor having a composite metal oxide can be controlled by a localized heater.

All in all, the present disclosure provides microelectronic electrochemical structures and related fabrication methods. A composite microelectronic structure is provided that includes first and second electrodes and heater elements dielectrically isolated from one another at a crossing thereof, the crossing surrounded by a dielectric material (e.g., $SiO_2$, $Si_3N_4$, etc.). A portion of the dielectric material around the crossing of the first and second electrodes is exposed and two or more layers of metal oxide materials are deposited such that the deposited metal oxide material contacts the exposed outer surfaces of the first and second electrodes.

The development of ultra-low power, high density, sensitive, reliable, selective and scalable gas sensor technology is critically needed for wearable health, internet of things (IoT), smart phones, and smart cities, since the environment around us, both outdoors and inside buildings, influences our health and lives directly through the air we breathe. For example, the World Health Organization (WHO) reported ambient air pollution has caused 4.2 million deaths and household air pollution has caused about 2.8 million deaths in 2016. In addition, human breath contains critical gaseous species that are indicators for disease like acetone, cardiac conditions, or cancers. Human skin is an ideal place to monitor state of health as skin vapor and skin sweat contain a range of important information related to the state of the body. Skin vapor analysis of volatile organic compounds (VOCs) offers a noninvasive, painless, and effective route for detection of biomarkers that originate from biological processes such as inflammation and microorganisms within the body.

Ultra-low power consumption is especially important as it enables long term monitoring of environmental pollutants in a small and/or wearable form factor leading to correlation of an individual's environmental exposure to their physiological status and prediction of health conditions like asthma and cardiovascular risks. Relying on air quality data from standard sensors installed by the U.S. Environmental Protection Agency is insufficient as they do not provide the necessary granularity for an individual personal environmental exposure as they are located at large distances away from each other. Technologies that measure air quality in microenvironments at any time and from any location are necessary. While many technologies for environmental/gas sensing are available in the commercial sector, such as mechanical, optical, magnetic, solid-state and electrochemical, none of these provide the best solutions for the above applications. For example, conventional electrochemical sensors are relatively accurate and reasonably selective but suffer from large size, surface poisoning, and long-term stability. Optical sensors provide a superior resolution but they are bulky and expensive. For low cost, high volume, and miniaturized gas sensing applications, semiconductor metal oxide (SMO) based sensors are a very attractive option. However, current SMO gas sensors face serious challenges because they require high temperature operation leading to high power consumption and reliability concern. It has been shown that metal oxide based gas sensors require high temperature operation (>200° C.) to activate the sensing layer, and hence, they are not suitable for wearable, portable, and continuous use. As an example, n-type metal oxide sensors ($SnO_2$, ZnO, and $WO_3$) need to be heated above 400° C. to discriminate common interfering gases like $NO_2$ and Ozone. This high temperature of operation also causes baseline drift and long-term instability.

In contrast, embodiments of the present disclosure enable a monolithically integrated sensor array with multiple gas detection capabilities in a small form factor (for example, 3 by 5 sensors array in 0.25 $mm^2$ area) resulting in substantial reduction in operating power and manufacturing cost. Such an integrated sensor platform will find many applications in the health sector such as breath sensing and skin vapor sensing, and in the IoT sector, such as smart cities and smart homes. Furthermore, they can be integrated into portable and wearable electronics to generate personalized data sets such that these personalized data sets contain spatial information as well as micro-exposure data to correlate to health.

In brief, the present disclosure describes embodiments for a highly scaled and monolithically integrated gas sensor array that can serve as a platform for (i) single chip environmental monitoring and (ii) low-power personal exposure and health monitoring. An exemplary gas sensor array features low power consumption, a small form factor, process compatibility to current high volume silicon foundry processing, and integration of various composite metal oxide sensing layers to sense multiple gas analytes. An exemplary novel platform is based on a combination of on-chip MEMS (Micro-Electro-Mechanical Systems) heater arrays and ultra-thin metal oxides such that a monolithic array of a multiple metal oxide sensing surfaces is produced. An exemplary monolithically integrated and densely packed array sensor platform has the potential for solving problems facing current sensors such as high power consumption, large active area, and size, selectivity, and reliability. In one embodiment, among others, the array can be monolithically fabricated to have at least 15 sensors in the same real estate as would be occupied by a single state-of-the-art MEMS sensor. In various embodiments, thin heater membranes, arranged into crossbar arrays, can be used for selective on-chip annealing to convert multi-layer metal oxide stacks into a multitude of sensing surfaces for various applications, such as empowering E-nose machine learning for detection of variety of gases (ozone, nitrogen dioxide, carbon monoxide, acetone, methanol, ethanol, isoprene, and formaldehyde) with desired specificity.

Embodiments of the present disclosure include highly sensitive and selective semiconductor metal oxide gas sensors. These include sensors for ozone, $NO_2$, and formaldehyde for environmental monitoring and NO, acetone, and volatile organic compounds for biomarker monitoring in breath and skin. Such embodiments, among others, are characterized by on-chip annealing capability for intermixing of two or more different metal oxide layered stacks to form composite oxide and for curing/cleaning of sensing surface. Heater structures for an exemplary environmental sensor have low power consumption and may operate in a static mode in various embodiments or can have a pulsed operation mode to minimize the power dissipation. Embodiments of the present disclosure can utilize reliable and robust heating electrode material that allows for an integration of current MEMS and CMOS structures and processes.

In accordance with embodiments of the present disclosure, the realization of an exemplary novel platform enables metal oxide-based sensing technology to be operated at low temperatures by monolithically integrated multiple sensing materials to detect multiple gases and integrating with CMOS/MEMS processing. This can lead to a highly disruptive sensing technology and enable adoption of gas sensors into various applications. Atomic layer deposition (ALD) is widely used thin film deposition system as it provides atomic scale films. Atomic layer deposition (ALD) can be utilized to form ultrathin multi-layer metal oxides and, by selective on-chip annealing, these multilayer stacks can be converted to variety of metal oxide surfaces of varying compositions based on the heater temperature. By varying the temperature of the various heaters, different regions of metal oxide surfaces can be created monolithically. This enables the ability to sense a variety of different gas analytes increasing selectivity at lower power consumption. By combining ALD metal oxide sensing layers with sensor array design, highly integrated, selective, and sensitive sensing layers can be realized. Current metal oxide gas sensing utilize a large area and single gas sensor surface. While metal oxide-based semiconductors can be viewed as sensitive sensing materials, they need to be heated more than 200° C. to activate the material. To lower the operating temperature, the combination of ALD metal oxide with graphene, 2-dimensional materials, and carbon nanotubes has been reported. However, these increase the process complexity, and thus, large-scale fabrication can be an issue. In accordance with embodiments of the present disclosure, an exemplary multiple metal oxides array platform solves the above mentioned issues.

Figure 7:
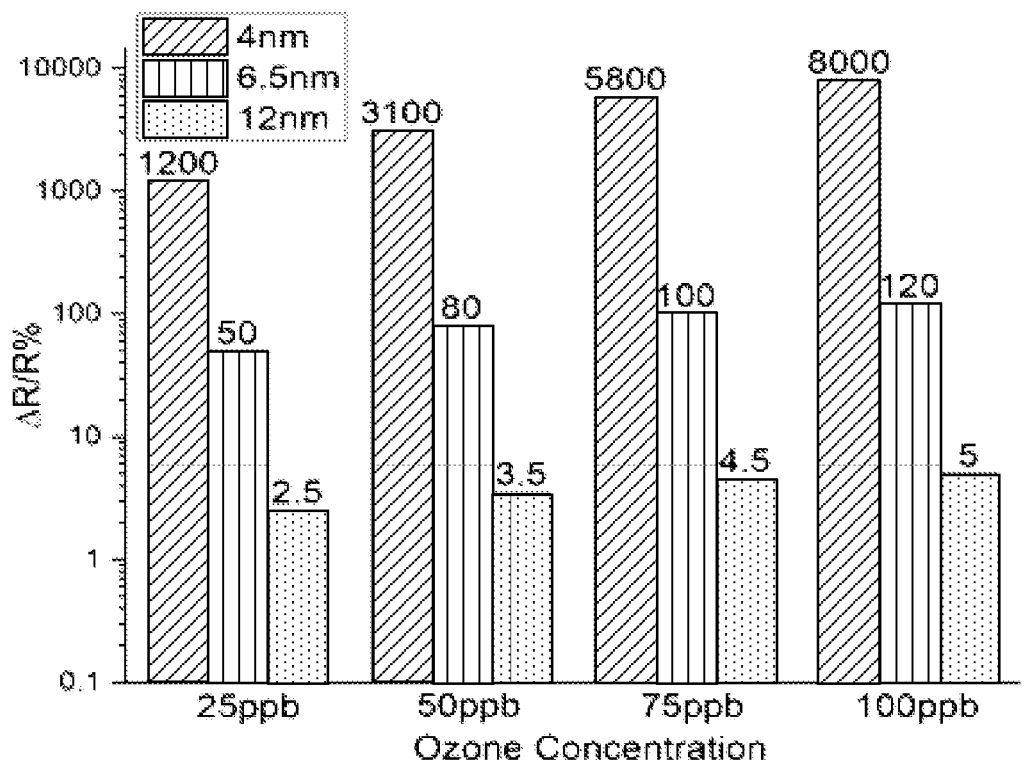
FIG. 7 shows a plot of a room temperature ozone response versus $SnO_2$ film thickness in accordance with the present disclosure.

In exemplary multiple metal oxide platform, ALD nanofilms based single metal oxide sensor can produce a selective and sensitive gas sensor which operates at room temperature (e.g. without heating) via engineering of the metal oxide thickness, as shown in FIG. 7 (which provides a plot of a room temperature ozone response versus $SnO_2$ film thickness). This approach has produced one of the lowest power consumption levels reported in literature (0.15 mW). Accordingly, FIG. 7 suggests that the sensitivity can be enhanced by engineering the film thickness which is more attractive than increasing sensing area to improve sensitivity. For example, in FIG. 7, 4 nm ALD $SnO_2$ shows a superior response compared to 12 nm ALD $SnO_2$.

Figure 8:
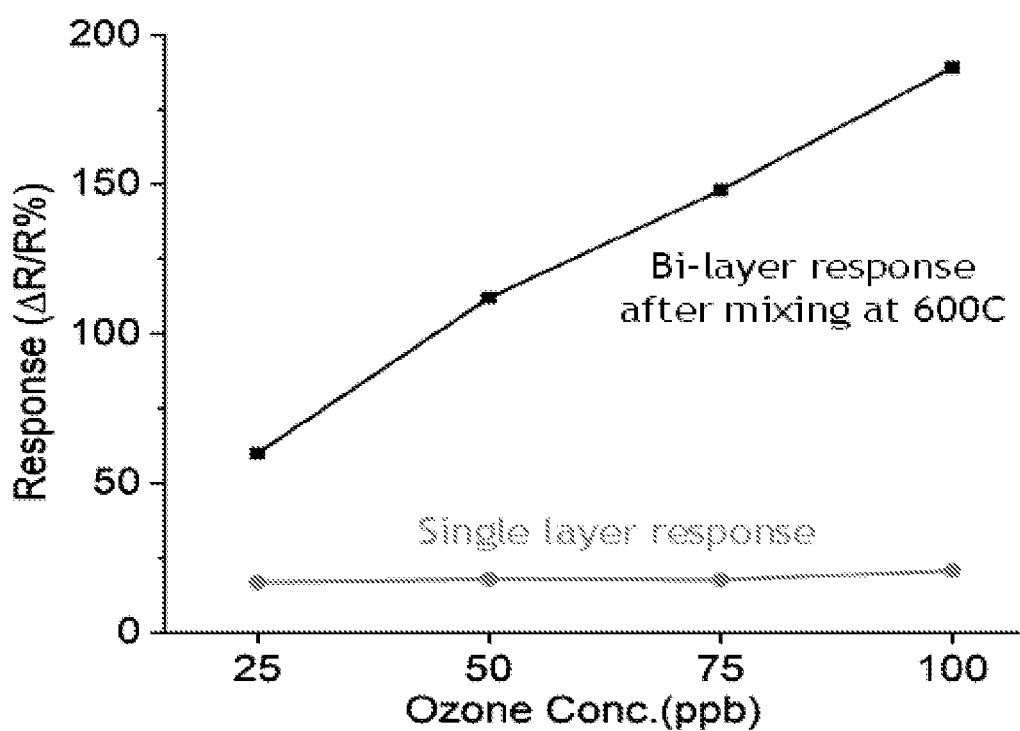
FIG. 8 shows a plot of a sensor response versus ozone concentration in accordance with the present disclosure.

While power consumption can be significantly reduced with an exemplary heater array approach combined with ALD metal oxide nanofilms, selectivity towards different gases remains a challenge for metal oxides and requires E-nose approaches utilizing machine learning to discern patterns for different gases. To achieve this, it is essential to create differences in the sensing process such as heating sensor layers to different temperatures (ideally using different heaters) or using different composition of metal oxide sensing layers that exhibit different responses to various gases of interest. Ideally, using both routes and supporting with machine learning provide the best selectivity performance. However, integration of different metal oxides in a single platform is quite challenging when considering traditional CMOS approaches as multiple discrete metal oxide sensors on a single chip will dramatically increase processing complexity, as it requires multiple deposition/etching steps that can in turn compromise the sensor surface integrity and increase cost. The combination of discrete metal oxides and composite oxides (two intermixed metal oxides) provides better selectivity and sensitivity. Composite oxides containing two metal cations have shown improved sensitivity over single oxides, as illustrated by FIG. 8 (which provides a plot of a sensor response versus ozone concentration) since sensing performance is controlled by interaction between a sensor surface and the target gas and by the ability to convert a surface charge into electrical signal. The introduction of a specific gas-sensitive oxide materials to the host oxide not only provides a chemical change at the gas interface inducing the sensitivity enhancement but also changes the state of grain boundaries resulting in the stability enhancement during the sensor operation. For example, FIG. 8 shows that a bi-layer response after mixing has an enhanced response to ozone as compared to a single layer response.

In accordance with embodiments of the present disclosure, an exemplary multiple oxide sensor platform not only produces a monolithic array of different metal oxide sensors but also enables individual sensors to be heated to different temperatures during operation such that each sensor has the best sensitivity. Low selectivity is one of the main disadvantages of the semiconductor metal oxide sensor. Composite oxides have shown improved selectivity over a single metal oxide sensor due to the catalytic effect or improvement of structural parameters. However, the complex fabrication methods of current composite oxides limit their use for thin film MEMS based gas sensor technology. It is very difficult to control the size and morphology of the oxide composites from run to run. Therefore, there is an urgent need for developing a new technology to form composite oxides that is compatible to current thin film MEMS processing.

In exemplary multiple metal oxide platform, MEMS array heaters are used for on-chip annealing of ALD multilayers in selected regions to intermix the ALD metal oxide layers to varying degrees. The area where only the original top layer is desired is not subjected to any on-chip anneal. A second area will be exposed to medium temperatures >~600° C. for and a third area will be exposed to even higher temperatures. These anneals are expected to intermix the three layers to varying degrees thereby producing different sensing surfaces. Hence, another key innovation of an exemplary approach is that a single metal oxide deposition step can produce multiple metal oxide surfaces that enable selective sensing. This on-chip annealing capability can also be used for recrystallization annealing to solve the lifetime issue of current metal oxide sensors due to the surface poisoning.

Figure 9:
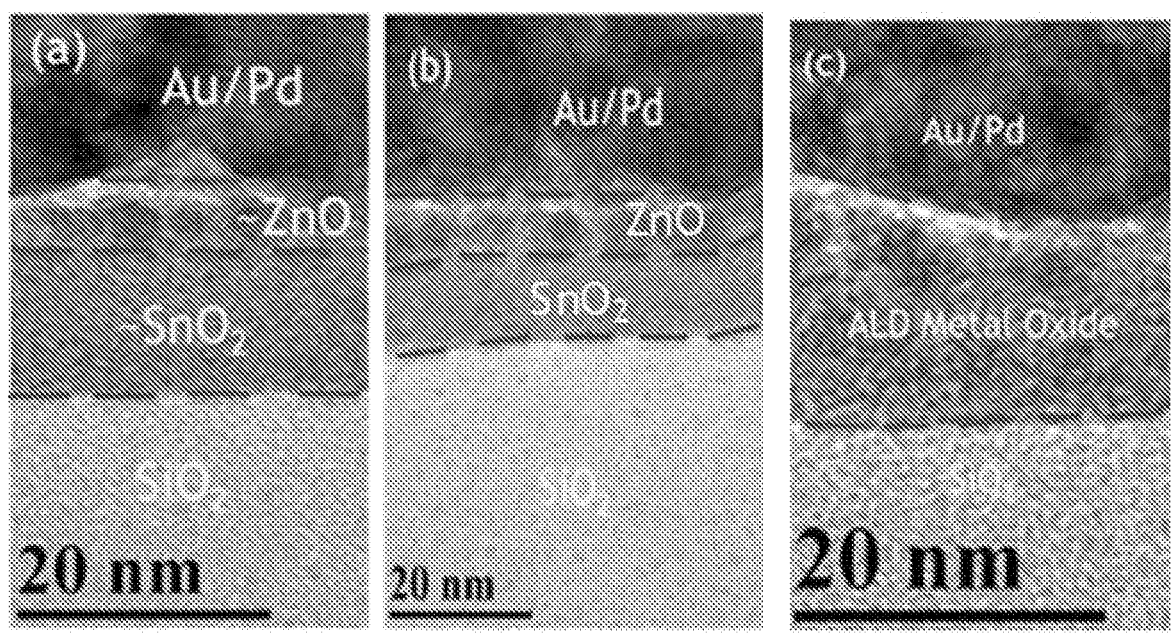
FIG. 9 presents TEM images of samples annealed at (left) 300° C., (middle) 600° C., and (right) 900° C. showing the intermixing between ultrathin $SnO_2$ and ZnO nanofilms through the on-chip heaters in accordance with various embodiments of the present disclosure.

The present disclosure has also recently explored intermixing of stacks of metal oxides formed by ALD, in which ALD deposited bi-layer $SnO_2$/ZnO were annealed at different temperatures. FIG. 9 presents TEM images of samples annealed at (left) 300° C., (middle) 600° C., and (right) 900° C. showing the intermixing between ultrathin $SnO_2$ and ZnO nanofilms through the on-chip heaters where the heater area is so small that rapid heating can be achieved. Since thermodynamics are different for each metal oxide, their surface reaction and chemical diffusion properties are important to determine the order of metal oxides stack in ALD deposition. This is due to the fact that the nanoscale kinetics are known to be different from bulk materials. The degree of intermixing depends on many factors such as thickness of the layers, temperature, order of the metal oxide layers and anneal ambient and these can be controlled by an exemplary array platform. The variation in composition of metal oxide surfaces produced by on-chip annealing provides the inherent variability that is essential for E-nose analysis. Therefore, an exemplary sensor array can provide a highly scaled and integrated platform resulting in transformative diversification of CMOS into advanced sensing applications.

It should be emphasized that the above-described embodiments of the present disclosure are merely possible examples of implementations, merely set forth for a clear understanding of the principles of the disclosure. Many variations and modifications may be made to the above-described embodiment(s) without departing substantially from the principles of the disclosure. All such modifications and variations are intended to be included herein within the scope of this disclosure and protected by the following claims.

The invention claimed is:
1. A method for sensing a change in an environment comprising:
  forming an array of multiple metal oxide materials on a substrate, wherein:
    at least one of the multiple metal oxide materials comprises a plurality of layers of different metal oxide materials;
    the multiple metal oxide materials are deposited on a cross-bar array of heater elements and electrodes;
    each row in the cross-bar array contains an independently-controlled heater element and each column in the array contains a pair of electrodes;
    at each crossing in the cross-bar array, one of the multiple metal oxide materials is deposited; and
    the pair of electrodes and the heater elements are dielectrically isolated from one another at each crossing; and
  applying a particular temperature to one of the multiple metal oxide materials by individually controlling a row of the heater elements on which the one of the multiple metal oxide materials is positioned, wherein the one of the multiple metal oxide materials intermixes the layers of different metal oxide materials at the particular temperature applied by the row of heater elements.

2. The method of claim 1, further comprising:
measuring a change in electrical resistance, surface ionization, optical, or magnetic parameters of the one of the multiple metal oxide materials, wherein the one of the multiple metal oxide materials is sensitive to a presence of a particular gas substance.

3. The method of claim 1, further comprising applying a different temperature to another one of the multiple metal oxide materials by individually controlling a different row of the heater elements on which the other one of the multiple metal oxide materials is positioned.

4. The method of claim 1, wherein the at least one of the multiple metal oxide materials is sensitive to a presence of a particular gas substance.

5. The method of claim 1, wherein the at least one of the multiple metal oxide materials is sensitive to a change in the environment from an exhaled breath.

6. The method of claim 1, wherein the at least one of the multiple metal oxide materials is sensitive to a change in the environment from a skin vapor.

7. The method of claim 1, wherein the substrate is a stretchable substrate formed of Nanocellulose.

8. The method of claim 1, wherein the array of multiple metal oxide materials comprise at least a first metal oxide material having first layers of metal oxide material and a second metal oxide material having second layers of metal oxide material that is different from the first layers of metal oxide material, wherein the first metal oxide material produces a response to a first analyte that is different from a response to the first analyte by the second metal oxide material, wherein a number of the first layers is different from a number of the second layers.

9. The method of claim 1, wherein the array of multiple metal oxide materials comprise at least a first metal oxide material having first layers of metal oxide material and a second metal oxide material having second layers of metal oxide material that is different from the first layers of metal oxide material, wherein the first metal oxide material produces a response to a first analyte that is different from a response to the first analyte by the second metal oxide material, wherein the first layers of metal oxide material is configured to be activated at a first temperature, wherein the second layers of metal oxide material is configured to be activated a second temperature that is different from the first temperature.

10. The method of claim 1, wherein the substrate is a single silicon wafer, wherein the array of multiple metal oxide materials on the substrate comprise at least 15 metal oxide gas sensors.

* * * * *